United States Patent
Rodgers

(12) United States Patent (10) Patent No.: US 7,124,669 B1
Rodgers (45) Date of Patent: Oct. 24, 2006

(54) METHODS EMPLOYING OPTICAL SOURCE AND OPTICAL SENSOR FOR DETECTING LIVING TISSUE WITHIN AN ANIMAL NAIL

(76) Inventor: Sandra J. Rodgers, 2983 Timberline, Eugene, OR (US) 97405

( * ) Notice: Subject to any disclaimer, the term of this patent is extended or adjusted under 35 U.S.C. 154(b) by 0 days.

(21) Appl. No.: 11/315,878

(22) Filed: Dec. 22, 2005

Related U.S. Application Data

(62) Division of application No. 10/246,071, filed on Sep. 17, 2002, now Pat. No. 7,000,321.

(51) Int. Cl.
*A45D 29/00* (2006.01)
*A01K 13/00* (2006.01)
*B26B 17/00* (2006.01)

(52) U.S. Cl. .................. 83/13; 30/29; 30/123; 30/145; 119/600; 600/310; 132/75.5; 340/573.1

(58) Field of Classification Search ............ 30/29, 30/123, 145, 26–28; 119/600; 606/163, 606/164; 600/476, 340, 477, 310; 132/75.5, 132/75.4; 362/119, 120; 356/432; 250/215, 250/221; 340/600, 573.1; 83/13

See application file for complete search history.

(56) References Cited

U.S. PATENT DOCUMENTS

| | | | |
|---|---|---|---|
| 2,955,354 A | 10/1960 | Laing | |
| 3,838,507 A | 10/1974 | Clark | |
| 3,845,553 A | 11/1974 | Fields | |
| 4,228,585 A | 10/1980 | Nelson | |
| 4,449,297 A | 5/1984 | Fuchs et al. | |
| 4,564,355 A | 1/1986 | Traiger et al. | |
| 4,810,875 A | 3/1989 | Wyatt | |
| 4,836,206 A | 6/1989 | Maxwell et al. | |
| 5,195,925 A | 3/1993 | Gorans | |
| 5,280,788 A | 1/1994 | Janes et al. | |
| 5,751,835 A | 5/1998 | Topping et al. | |
| 5,772,597 A | 6/1998 | Goldberger et al. | |
| 5,987,346 A | 11/1999 | Benaron et al. | |
| 6,276,933 B1 | 8/2001 | Melnyk et al. | |
| 6,332,431 B1 | 12/2001 | Brown | |
| 6,388,247 B1 | 5/2002 | Asada et al. | |
| 6,553,592 B1 | 4/2003 | Yang et al. | |
| 6,865,812 B1 | 3/2005 | Martin | |
| 7,000,321 B1 * | 2/2006 | Rodgers | ........................ 30/29 |

* cited by examiner

*Primary Examiner*—Timothy V. Eley
*Assistant Examiner*—Jason Prone
(74) *Attorney, Agent, or Firm*—David S. Alavi

(57) ABSTRACT

An optical source illuminates a portion of an animal nail, and an optical sensor receives light from the illuminated portion. A processor generates a signal level, and differentiates between a "quick" signal level range (arising from illuminated living tissue in the nail) and a "nail" signal level range (arising from illuminating a nail portion with no living tissue). An indicator informs a user when the signal level is in the quick or nail range, determining the location of living tissue within the nail. Source(s) and sensor(s) may be mounted on an animal nail clipper, with illumination by the source and collection of light for receiving by the sensor occurring at a position relative to a blade so that when the signal level is within the nail range and the clipper is actuated to cut the nail, cutting of the living-tissue-containing portion of the animal nail is avoided.

20 Claims, 5 Drawing Sheets

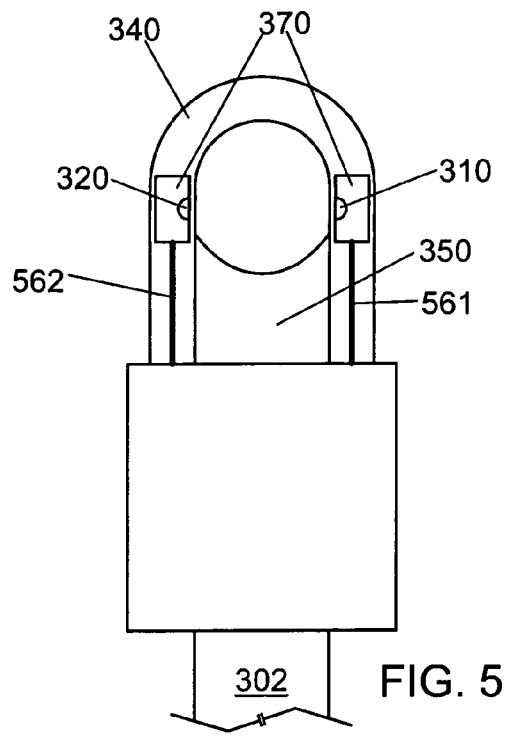 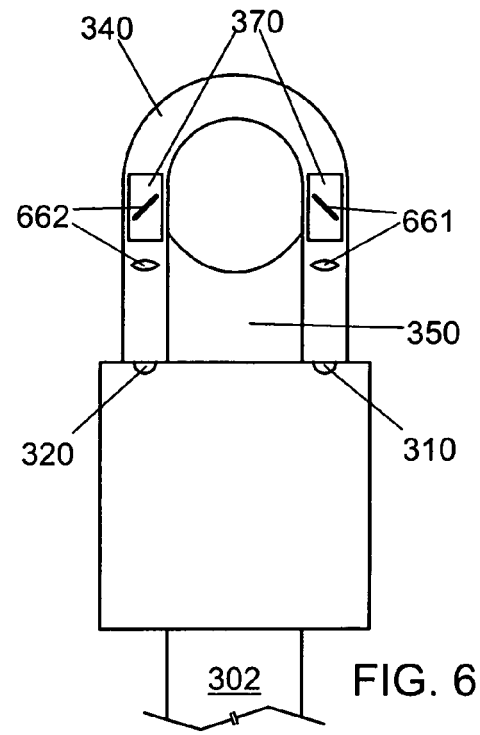
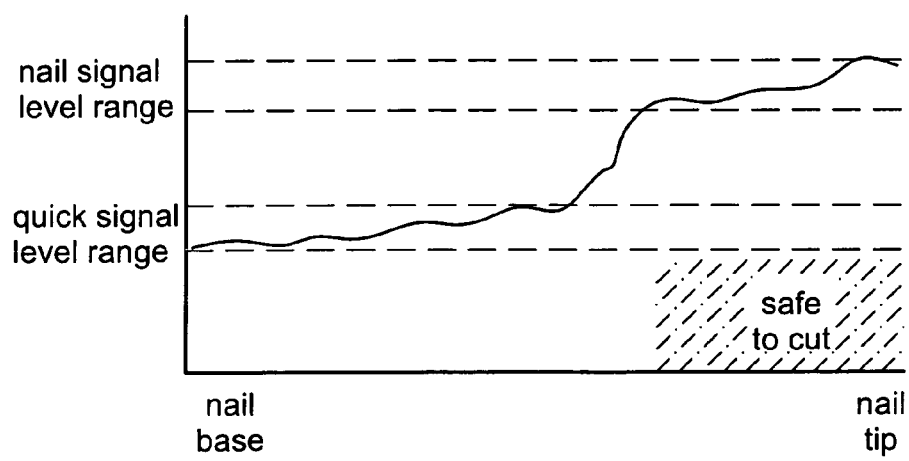
FIG. 8

US 7,124,669 B1

METHODS EMPLOYING OPTICAL SOURCE AND OPTICAL SENSOR FOR DETECTING LIVING TISSUE WITHIN AN ANIMAL NAIL

BENEFIT CLAIMS TO RELATED APPLICATIONS

This application is a divisional of U.S. non-provisional application Ser. No. 10/246,071 entitled "Optical source and sensor for detecting living tissue within an animal nail" filed Sep. 17, 2002 in the name of Sandra J. Rodgers, now U.S. Pat. No. 7,000,321 B1 said application being hereby incorporated by reference as if fully set forth herein.

BACKGROUND

The field of the present invention relates to animal grooming and care. In particular, an optical source and sensor are described herein for determining the location of living tissue within an animal nail.

Trimming or clipping animal nails is a routine task of pet care. Unfortunately, it may also be a problematic ordeal, owing to the common occurrence of "cutting the quick". The quick is the tip of the animal's digit, comprising living tissue, that extends into the animal's nail. While the nail comprises dead tissue and clipping it causes the animal no discomfort, inadvertently cutting the nail too short and also cutting the quick results in pain and bleeding for the animal, and distress for the pet owner. For animals with clear or translucent nails, it may be possible to see the quick, thereby avoiding it when cutting the nail. Many animals have one or more dark colored nails, making it nearly impossible to see the quick with the naked eye. It is nevertheless possible to use light to sense the end of the quick within the nail, and thereby position the clipper for cutting the nail without also cutting the quick.

It is therefore desirable to provide an optical source and sensor for an animal nail clipper for enabling a user to reliably position the clipper for cutting the nail without also cutting the quick. More generally, it is desirable to provide apparatus and methods for determining the location of living tissue within an animal nail for a variety of purposes related to pet grooming, pet care, and/or veterinary procedures, both diagnostic and therapeutic.

SUMMARY

Certain aspects of the present invention may overcome one or more aforementioned drawbacks of the previous art and/or advance the state-of-the-art of animal care, animal grooming, veterinary diagnosis, and/or veterinary therapy.

An animal nail clipper implemented according to the present invention comprises: at least one blade for cutting the nail, at least one optical source for illuminating a portion of the nail, and at least one optical sensor for receiving light from the illuminated portion of the nail. A processor generates a signal level from the optical sensor, and differentiates between a "quick" signal level and a "nail" signal level. The quick signal level arises from an illuminated living-tissue-containing portion of the animal nail, while the nail signal level arises from an illuminated portion of the nail substantially devoid of living tissue. An indicator informs a user of the clipper which of the quick signal level and the nail signal level (or some signal level between) is generated by the processor. Illumination by the optical source and collection of light for receiving by the optical sensor occurs at a position relative to the blade so that when the nail signal level is generated by the processor and the clipper is actuated to cut the nail, cutting of the living-tissue-containing portion of the animal nail is substantially avoided.

The optical source and sensor may be mounted directly on the clipper or may be coupled to the clipper by optical fibers. A variety of narrowband and/or broadband light sources may be employed, and detection may be wavelength-selective. One or more wavelengths may be chosen for enhancing the ability to differentiate quick from nail. A variety of processing schemes may be employed for generating a signal level from the optical sensor, and a variety of indicator schemes may be employed including a binary indicator (cut v. no cut) or a level indicator.

An optical source and sensor (with or without a blade) may be employed for determining the location of living tissue within the animal nail for other purposes as well, including diagnostic and/or therapeutic veterinary procedures. Additional objects and advantages of the present invention may become apparent upon referring to the preferred and alternative embodiments of the present invention as illustrated in the drawings and described in the following written description and/or claims.

BRIEF DESCRIPTION OF THE DRAWINGS

FIG. 5 is a top view of animal nail clippers implemented according to the present invention.

FIG. 6 is a top view of animal nail clippers implemented according to the present invention.

FIG. 8 shows an example of the dependence of signal level on longitudinal position along the nail according to the present invention.

In the Figures, various dimensions and/or proportions shown may be distorted for clarity. The embodiments shown in the Figures are exemplary, and should not be construed as limiting the scope of inventive concepts disclosed and/or claimed herein.

DETAILED DESCRIPTION OF EMBODIMENTS

Figure 1A:
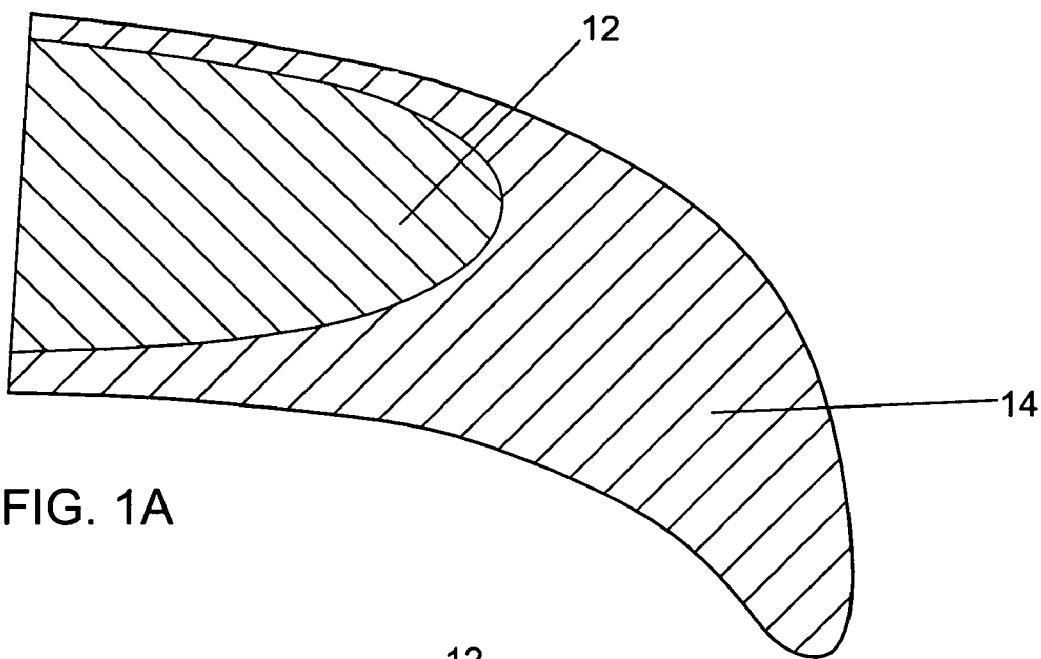
FIGS. 1A and 1B are schematic side and top cross-sections, respectively, of an animal nail.
Figure 1B:
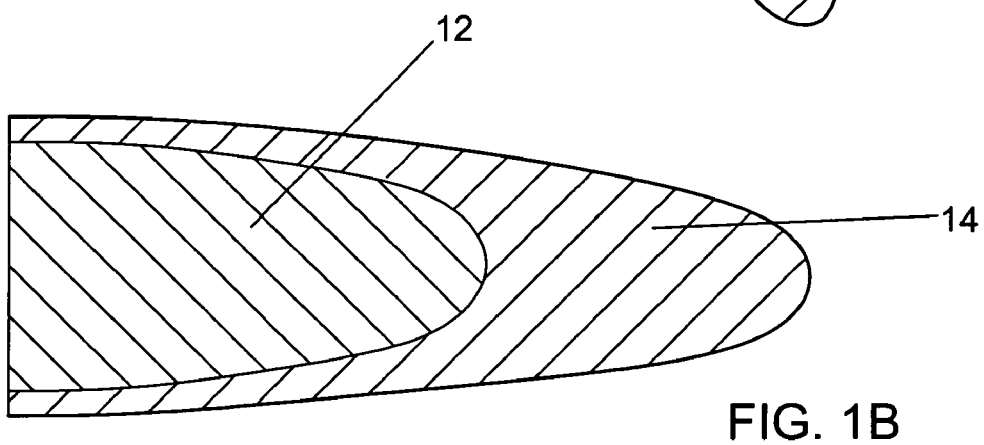

FIGS. 1A and 1B are schematic cross-sectional views of an animal digit and nail. The end of the digit comprises protruding living tissue referred to as the quick 12, surrounded by dead tissue that forms the nail 14. The portion of nail 14 extending beyond the quick 12 is the portion to be trimmed, preferably without cutting into the quick and causing pain and bleeding.

Figure 2:
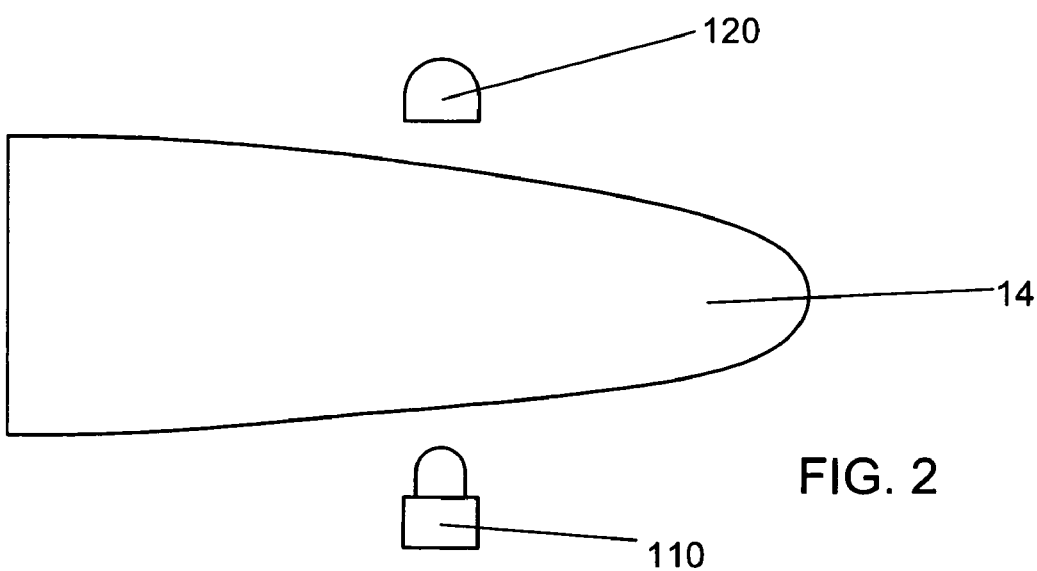
FIG. 2 is a schematic top view of an optical source and sensor implemented according to the present invention.

FIG. 2 schematically illustrates a general approach for detecting living tissue within the animal nail according to the present invention. An optical source 110 (equivalently, excitation source) emits light, some of which enters the nail 14. An optical sensor 120 (equivalently, collector) is placed at approximately the same longitudinal position along the nail 14. While shown across the nail from the optical source in FIG. 2, the optical sensor 120 may be placed anywhere around the circumference of the nail relative to the light source 110. Some portion of the light emitted from optical source 110 and entering the nail 14 will reach optical sensor 120 and be detected. The amount of light reaching optical sensor 120 depends on wavelength(s), detection geometry, and the nature of the tissue through which the light propagates (predominantly by scattering). Detection of this collected light, conversion thereof into one or more electrical signals, and analysis of the electrical signal(s) may be used for determining the location of living tissue within the animal nail. A nail trimmer may be placed (relative to the optical source and sensor) at a position beyond the quick to avoid cutting thereof, or some other veterinary procedure may be performed that depends on the location of living tissue within the nail.

Figure 3A:
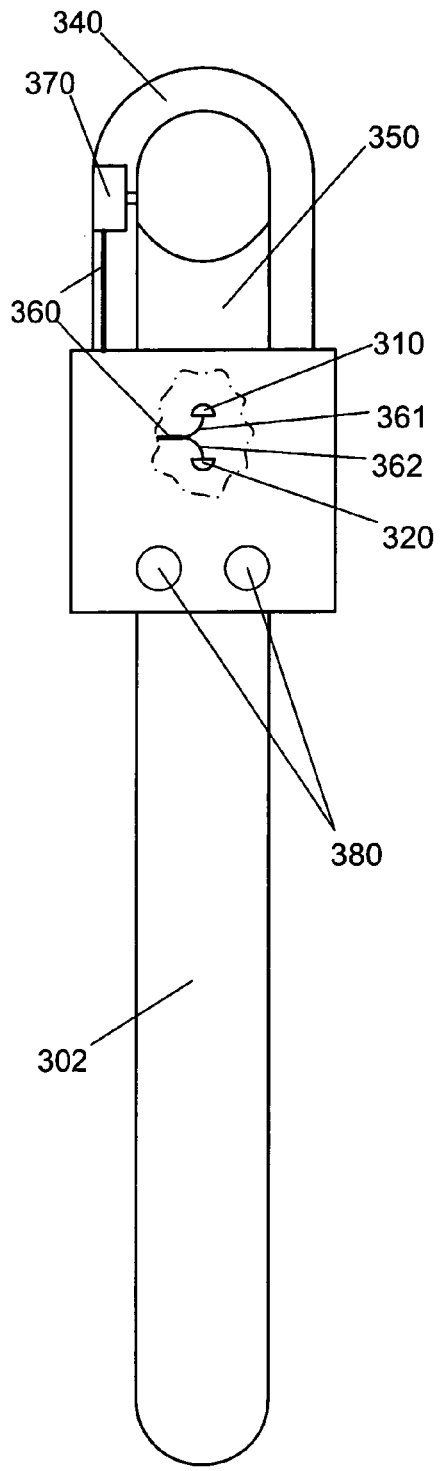
FIGS. 3A, 3B, and 3C are top, side, and schematic views of an animal nail clipper implemented according to the present invention.
Figure 3B:
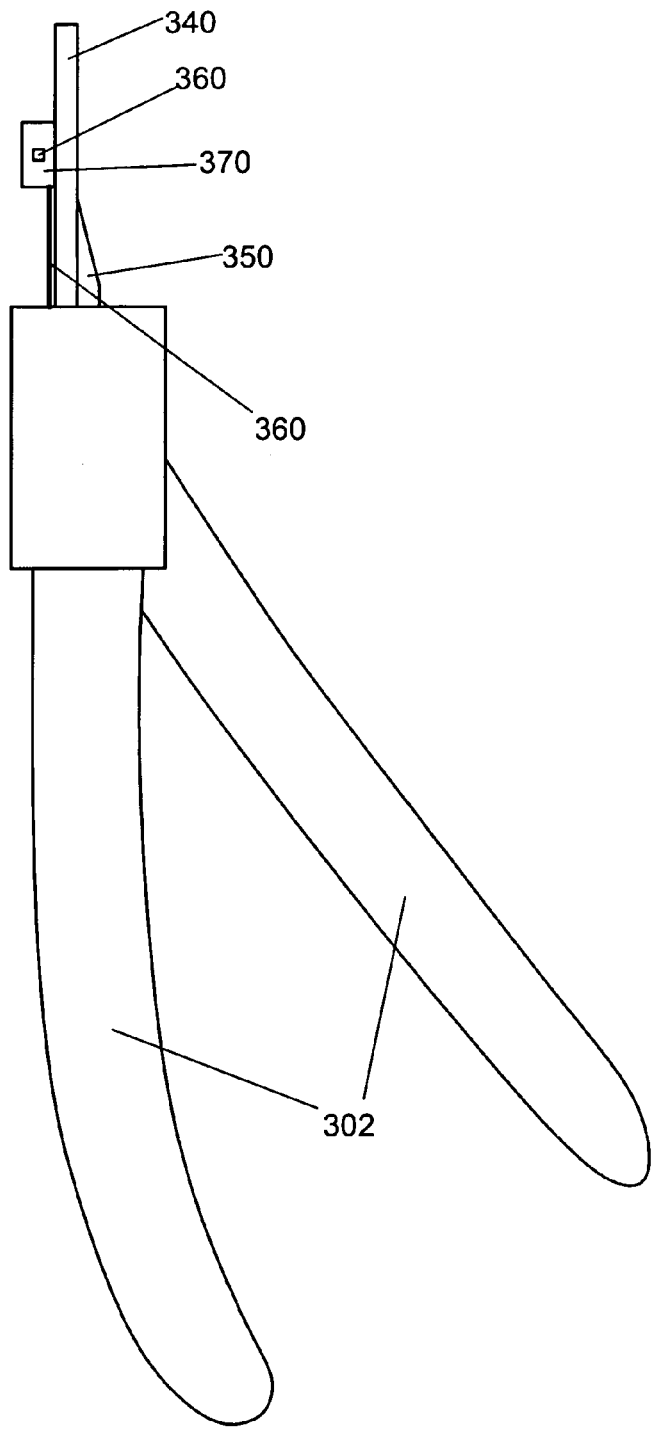

An exemplary embodiment of an animal nail trimmer according to the present invention is shown in FIGS. 3A (top view), 3B (side view), and 3C (schematic block diagram). A standard guillotine-type animal nail clipper is shown, including handles 302, a nail-retaining ring 340, and blade 350. During actuation of such nail clippers the nail-retaining ring may move to force the nail onto a substantially stationary blade, a moving blade may cut the nail held by a substantially stationary ring, or both blade and ring may move to cut the nail. The present invention may be implemented with any of these configurations of guillotine-type nail clippers. An optical source 310 and optical sensor 320 are positioned on or within handle 302 (shown through the cut-out portion of FIG. 3A), and are each optically coupled to a proximal end of a bundle 360 of two or more optical fibers. The optical source 310 may also be referred to as an excitation or scattering source. The distal end of the fiber bundle 360 may be positioned substantially transversely aligned with an inner surface of ring 340 so as to be in close proximity to an animal nail inserted therethrough for trimming. Fiber bundle 360 may include at least one source fiber 361, coupled at its proximal end for receiving light from the optical source 310 and delivering the light to the nail at the distal end of fiber 361. Fiber bundle 360 may also include at least one sensor fiber 362 (equivalently, collection fiber) for collecting light from the nail at the distal fiber end and transmitting at least a portion of the collected light to the optical sensor 320. Multiple collection fibers may be employed for increasing the amount of light collected. One or more spacers 370 may be employed for providing a fixed longitudinal offset or displacement between the blade 350 and the emission point for optical source 310 and the collection point for sensor 320. In this way, when the end of the quick is located using the optical source and sensor, the blade 350 is at a position beyond the end of the quick to avoid cutting thereof.

Figure 3C:
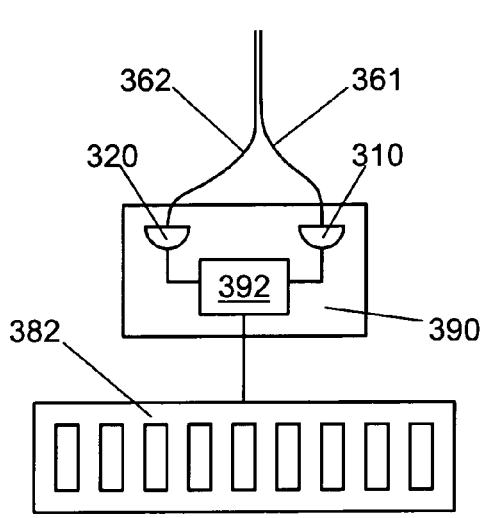

Optical source 310 and optical sensor 320 may preferably be included in a common electronic module 390 which may also include a power source (a battery of any other suitable power source; not shown), signal analysis component(s) 392, and an indicator for notifying the user whether the nail may be clipped without cutting the quick (indicator lights 380 in FIG. 3A; indicator bar graph 382 in FIG. 3C; other indicators may be equivalently employed). One or more of these may alternatively be provided as separate component (s). An electronic module may be sufficiently miniaturized so as to fit within the handle of the nail trimmer, or may be provided as a separate unit with electrical wiring and/or optical fiber connection(s) to the nail trimmer. The amount of scattered excitation light that reaches the detector depends on the excitation/collection geometry, the wavelength(s) of the excitation light, the collection efficiency, and the nature of the tissue being illuminated. It is typically the case that at one or more wavelengths, the amount of scattered light reaching the optical sensor differs between dead tissue (i.e., the nail) and living tissue (i.e., the quick), even when the nail is dark colored (brown or black, for example). Based on such tissue selectivity, the signal analysis components may be configured, programmed, and/or calibrated for distinguishing between a nail signal level and a quick signal level and for controlling the indicator. The indicator may be a simple binary indicator (cut v. no-cut), or may be a continuous or discrete level indicator that may show multiple signal levels at least spanning a range that includes the nail signal level and the quick signal level. The indicator may be one or more lights 380 (green=cut and red=no-cut, for example), a bar graph 382, a dial, a gauge, a readout, an audible indicator, text, or any other suitable indicator for conveying to the user a signal level and/or notifying the user whether it is safe to cut the nail without cutting the quick.

Figure 4A:
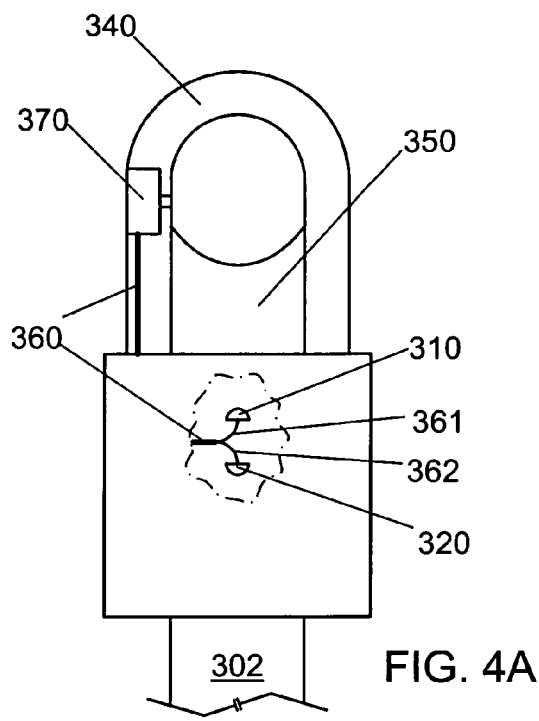
FIGS. 4A, 4B, and 4C are top views of animal nail clippers implemented according to the present invention.
Figure 4B:
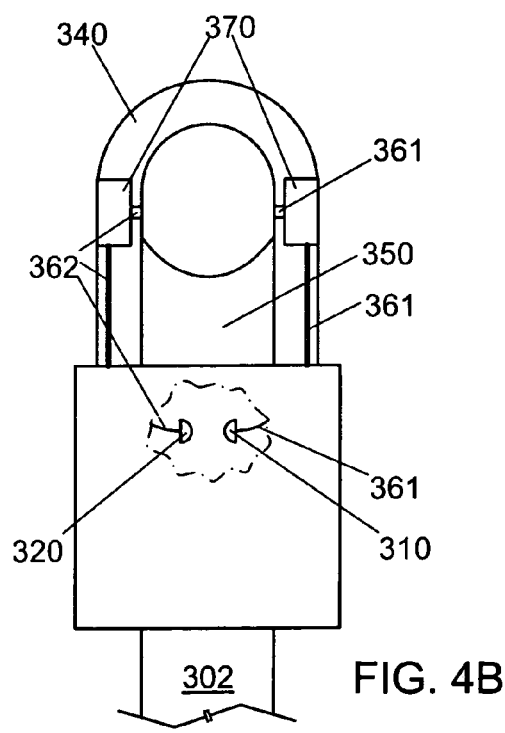
Figure 4C:
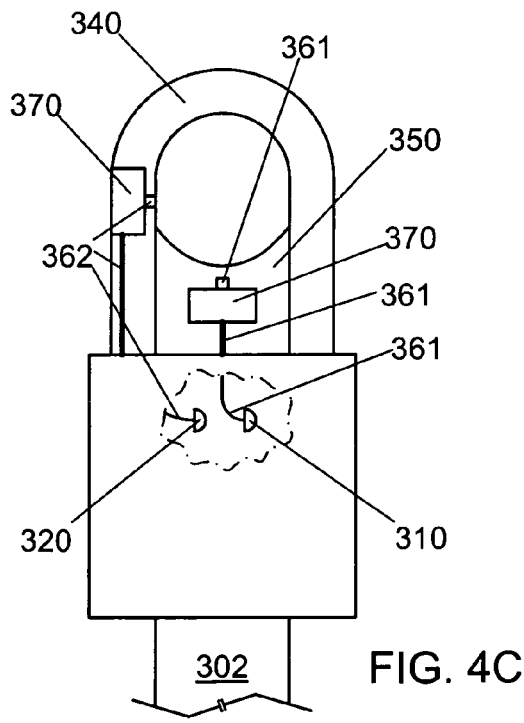

A wide variety of optical sources, optical detectors, light delivery and/or signal collection schemes, detection geometries, signal analysis, and/or calibration schemes may be employed while remaining within the scope of the present invention. For example, with source fiber 361 and collection fiber 362 in a common optical fiber bundle 360, the collection geometry is a back-scatter or reflectance geometry (FIGS. 3A/3B/3C and 4A), with scattered/reflected light being collected that propagates predominantly in a direction opposite the propagation direction of the source or excitation light. Other geometries may be equivalently employed, including a transmissive geometry having collected light propagating through the nail from the excitation source (FIGS. 2 and 4B), and a side-collection geometry having collected light propagating substantially at a right angle to the excitation light (FIG. 4C; other angles may be employed). In any of these geometries, the amount of light reaching the optical sensor depends on the wavelength(s) and the nature of the tissue being illuminated by the optical source. Optical fibers may provide a convenient way to position effective optical source(s) and/or optical sensor(s) in any desired geometry, by placing a distal end thereof (emitting end for a source; collection end for a sensor) at the appropriate excitation and/or collection position(s) around the ring longitudinally offset from the blade by the spacer. In another embodiment of the present invention, optical source (s) 310 and/or optical sensor(s) 320 may be placed directly at the appropriate excitation and/or collection positions on ring 340 or spacer 370 and connected to an electronic module (not shown) by source wiring 561 and sensor wiring 562 (FIG. 5). In another embodiment of the present invention, optical source(s) 310 and/or optical sensor(s) 320 may be positioned away from ring 340 and/or spacer 370, with one or more source optical components 661 being used to direct excitation light from the source 310 to the nail and/or with one or more sensor optical components 662 being used to direct collected light from the nail to the optical sensor 320 (FIG. 6). The source and sensor optical components may be separate, as in FIG. 6, or a common set of components may serve both source and sensor.

A variety of light sources may be employed for implementing the present invention. Solid-state light sources may enable sufficiently small and low-power light sources that may be implemented within a self-contained nail trimmer. Such solid-state sources may include semiconductor lasers and one- or multi-color light-emitting diodes (LEDs). Such solid-state optical sources may be made small enough to be mounted on an electronic control module (and fiber-coupled) within the handle or mounted directly on the ring or spacer. Other sources may be equivalently employed, such as white-light sources, other broadband optical sources, lamps of various sorts, incandescent sources, fluorescent sources, and so forth. Optical sources having relatively narrow spectral width (less than a few tens of nanometers, for example; referred to herein as narrowband sources) may be provided directly by sources with optical output of such spectral width (such as lasers and LEDs, for example), or alternatively may be produced by a white-light or other broadband source followed by one or more spectrally selective optical elements (one or more optical filters or a spectrometer, for example). Such spectrally-selective elements may be positioned before the nail (as part of the optical source, to restrict the spectral width of the excitation light) and/or after the nail (as part of the optical sensor, to restrict the spectral width of the collected light). Such spectrally-selective components may be configured so as to use a single nominal wavelength, or may use multiple spectral components (either simultaneously or consecutively).

Any suitable optical sensor may be employed for implementing the present invention. A photodiode or other solid state photodetector may be employed and may be sufficiently small for implementing within a self-contained nail trimmer, either on an electronic module and fiber-coupled, or mounted directly on the ring or spacer. A photovoltaic or photoconductive detector may be employed. Any other suitable photodetector may also be employed while remaining within the scope of the present invention.

A variety of detection and/or signal processing schemes may be employed for generating a signal level for determining whether the nail may be safely cut without also cutting the quick. Some schemes may require user calibration or other relatively high level of user interaction, while other schemes may be relatively independent of the user. Wavelength-dependent absorption and/or scattering of the nail may be exploited for differentiating living and dead tissue, or the intensity of the scattering at a single wavelength may be employed. The choice of detection scheme may dictate the number and/or type of light source(s), the number and/or type of photodetector(s), the number and/or type of wavelength-selective element(s), and/or the signal processing required for determining whether it is safe to cut the nail without also cutting the quick.

Various signal processing schemes may be employed for converting light collected by the sensor into a useful signal level. In the simplest scheme, the photodetector simply converts the collected light into an electrical signal, without regard to the source of the collected light. This scheme is the simplest to implement, but stray or ambient light, for example, may alter the measured signal level and complicate the location of the end of the quick by the user. Various methods may be employed for discriminating between ambient light and scattered light arising from the light source. In one example, the light source may be pulsed, and the photodetector signal might be temporally gated, so that the photodetector signal is used only during the time that the light source is on and thereby reducing the amount of ambient light contributing to the signal level. The optical source may be modulated at a reference frequency, and the reference frequency used for synchronous or phase-sensitive detection of the photodetector signal. Since ambient light would not be modulated at the frequency and phase of the reference, it would contribute negligibly to the signal level. If only a restricted wavelength range is used for the excitation source (narrowband excitation; see below), then a sensor wavelength filter or spectrometer may be employed for rejecting collected light outside of the range of interest, once again reducing the amount of ambient light contributing to the signal level. Other suitable methods for increasing signal-to-background may be employed while remaining within the scope of inventive concepts disclosed and/or claimed herein.

Figure 7A:
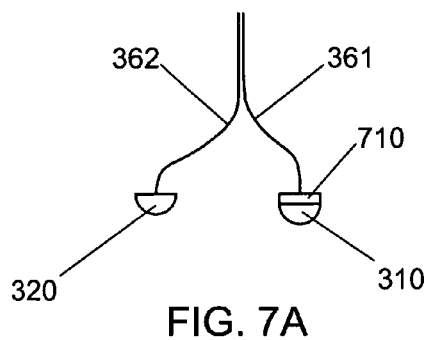
FIGS. 7A, 7B, 7C, 7D, 7E, and 7F are schematic diagrams of multi-wavelength detection schemes implemented according to the present invention.
Figure 7B:
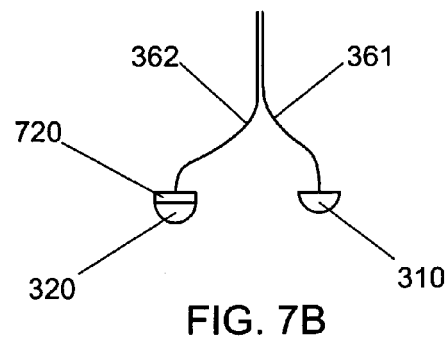

The ability to find the end of the quick within the nail is influenced by the wavelength employed. White-light or other broadband source and/or sensor may offer limited tissue selectivity for finding the end of the quick. By restricting the source and/or the sensor to a relatively narrow wavelength range (i.e., narrowband measurement) having an enhanced absorption and/or scattering differential between the nail and the quick relative to other wavelength ranges, the ability to find the end of the quick may be enhanced. For example, blood (present in living tissue) tends to absorb strongly in several visible/near-IR wavelength ranges, including around 420 nm, 500–600 nm, and 650–950 nm. Dead tissue of the nail may not absorb as strongly at such wavelengths, so that these wavelengths may exhibit enhanced dead tissue v. living tissue selectivity. Other wavelengths exhibiting an enhanced scattering and/or absorption differential between living tissue of the quick and dead tissue of the nail may be equivalently employed. The signal differential between nail and quick may therefore be enhanced relative to a wavelength range scattered/absorbed substantially similarly by quick and nail. Use of a particular wavelength or wavelength range may be accomplished by employing a narrowband source 310 (such as a laser or LED), or by employing a white-light or other broadband source 310 along with a spectral filter, spectrometer, or other wavelength-selective component (on one or both of the source and the sensor). FIG. 7A shows a broadband source 310 and a source filter 710, while FIG. 7B shows a sensor filter 720.

A simple detection scheme would include a single light source (which may be broadband or narrowband, as discussed above) and a single detector. The absolute signal level (which may be normalized relative to the optical source output, to account for optical source variations) may be used to determine whether the source and sensor (and therefore the nail clipper) is beyond the quick. The signal level produced by the collected light will vary along the length of the nail, and typically exhibits a transition at the end of the quick (FIG. 8, which shows an exemplary trace of signal v. nail position in which the signal level due to collected light is lower over the quick). The sharpness of this transition between a quick signal level range and a nail signal level range is limited by several factors, including the size and separation of the source and sensor near the nail surface, the distance between the nail surface and the source/sensor, the wavelength employed, the amount of ambient light contributing to the signal level, and the size of the nail and quick signal level ranges relative to their difference. For sufficiently accurate positioning, for example, the difference between nominal nail and quick signal levels is preferably large enough that the respective signal level ranges do not substantially overlap. For a fiber bundle as shown in FIGS. 3A/3B/3C, illumination and collection may effectively be within a millimeter or less of each other, and may be within a millimeter or less of the nail surface (or in contact with the nail). In such a configuration, the end of the quick may be located within a precision of 1–2 millimeters. Other spacer sizes may be employed as appropriate for particular source/sensor sizes and detection geometry. The thickness of the spacer may be made one or more millimeters wide, so as to position the blade beyond the uncertainty range of the end of the quick, thereby ensuring that the quick is not cut along with the nail. The absolute signal level may be influenced by various factors during use, such as ambient light, the nail color, the position of the source/sensor relative to the nail (both distance from the nail surface and orientation relative to the nail). Due to this variation, it may not be possible or desirable to set an absolute signal level ahead of time for determining when it is safe to cut the nail.

It may be preferable to implement a calibration procedure, which may be a one-time procedure to prepare the nail clipper for initial use, or may be a procedure performed with each use of the nail clipper. In an example of the latter type of procedure, for each nail a user might take signal measurements at positions near the nail tip and then as far along the nail (away from the tip, toward the base of the nail) as possible. These measurements may then serve as baselines (nail signal level range and quick signal level range, respectively; FIG. 8) against which to compare signal levels measured at intermediate points along the nail. The nail may then be safely cut at a point just beyond the transition from the quick signal level range to the nail signal level range. These baseline or reference signal levels/ranges may be stored by the electronic module and used to generate a cut/no-cut indicator (using a level-discriminator or other similar processing component), or alternatively the signal level may be continuously displayed by a bar graph or similar level indicator for guiding the user to an appropriate cutting position. In either case, the mounting of the source and sensor directly on the clipper (with a suitable spacer) enables reliable positioning of the clipper for cutting the nail without also cutting the quick. It may be desirable to provide processor components for enabling adjustment of signal levels that correspond to various readouts. It may be necessary to adjust the range of signals corresponding to the ends of a bar graph or to "cut" and "no-cut" indications for different animal nails, differing measurement conditions, and/or to account for variations in light sources, power sources, and/or detectors.

Multiple-wavelength detection schemes may further enhance the ability to locate the end of the quick within the nail. Instead of relying on a single signal level as in the previous examples, which may be susceptible to variations in the manner in which the measurements are taken, a ratio or difference of signal levels obtained at differing wavelengths may be employed to determine the presence or absence of living quick tissue. For example, one wavelength (or relatively narrow wavelength range) may be chosen having a substantial scattering/absorption differential between quick and nail, while a second wavelength (or range) may be chosen having a smaller or insubstantial differential, or having a differential of the opposite sign. A ratio or difference between collected signals at the two wavelengths (which may each be normalized relative to the respective optical source output) should therefore be somewhat independent of the precise positioning of the clipper relative to the nail surface, or to ambient light levels, particularly in a back-scatter collection geometry. User calibration procedures (one-time or every-time calibration; see discussion above) may be used for locating the end of the quick using ratios/differences of signal levels. However, by using a ratio or difference of signals arising from different wavelengths, the source/sensor may instead be calibrated ahead of time, which would enable a cut/no-cut indication upon a first measurement on a nail, and would substantially eliminate user judgment from the process of locating the end of the quick.

Figure 7C:
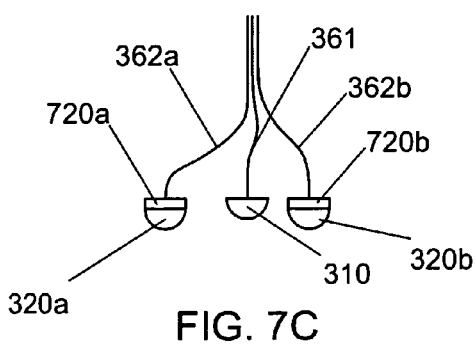
Figure 7D:
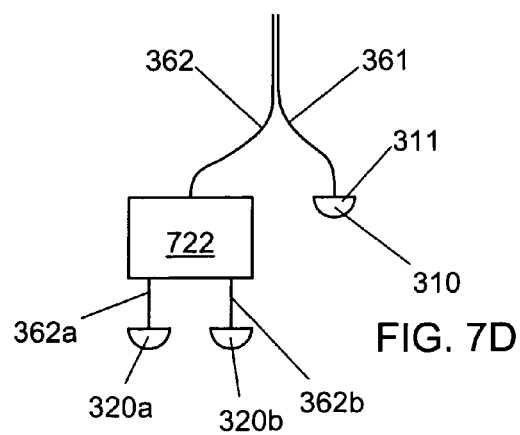
Figure 7E:
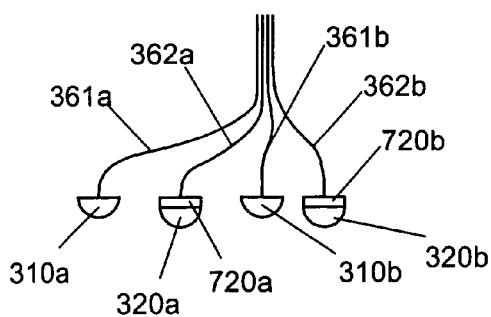
Figure 7F:
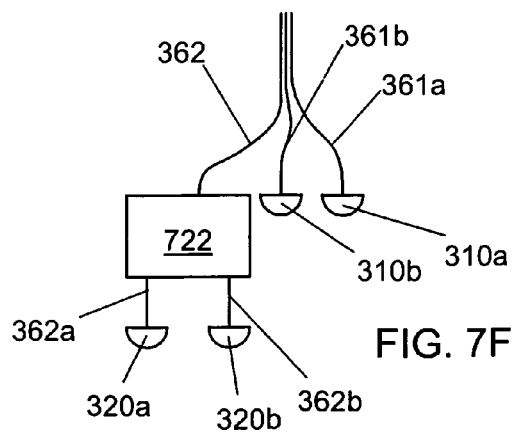

Multiple-wavelength embodiments of the present invention may be implemented in a variety of ways. A single optical source 310 (white-light source, other broadband light source [broadband here meaning broad enough to span the desired wavelengths], or multiple-wavelength source [a combination LED chip that emits at two distinct wavelengths, for example]) may be employed, and separate photodetectors 320*a*/320*b* (coupled through optical fibers 362*a*/362*b*) employed for each collected wavelength (FIGS. 7C and 7D). These separate photodetectors may be each provided with a corresponding optical bandpass filter 720*a*/720*b* for selecting the desired wavelength (FIG. 7C), or alternatively a spectrometer 722 or other dispersing device may be employed (FIG. 7D), with the photodetectors 320*a*/320*b* each positioned to receive the appropriate wavelength therefrom. Instead of a white-light, other broadband, or multiple-wavelength source, multiple light sources 310*a*/310*b* (coupled through optical fibers 361*a*/361*b*) emitting at the multiple desired wavelengths may be employed (multiple lasers or LEDs, for example), with the scattered light collected through filters 720*a*/720*b* (FIG. 7E) or a spectrometer 722 (FIG. 7F) as described above for detection by multiple photodetectors 320*a*/320*b*. Alternatively, a single detector may be employed for detecting multiple wavelengths derived from multiple sources (not shown). The multiple sources may be alternately pulsed, and the signal processor gated for separating the photodetector signals arising from the two wavelengths. Alternatively, the multiple sources could be independently modulated (with differing frequencies and/or phases) and corresponding reference signals generated for independent synchronous or phase-sensitive detection of photodetector signals arising from each wavelength component. Other detection/processing schemes for detecting multiple scattered wavelengths could equivalently be employed while remaining within the scope of inventive concepts disclosed and/or claimed herein.

In addition to guillotine-type animal nail clippers, the present invention may be implemented for scissor-type nail clippers or any other type of nail clipper. Scissor-type nail clippers may be implemented according to the present invention, including an optical source and sensor positioned on one of the blades with a spacer. As in the case of the guillotine-type clippers, the spacer ensures that the nail is clipped at a point beyond the end of the quick in spite of the measurement uncertainty of that location. A back-scatter geometry may be preferred for a scissor-type embodiment of the present invention, since the measurement would be independent of the degree to which the scissors are opened. In a transmission geometry with source on one blade and sensor on the other, the signal level would vary just by opening and closing the scissors, adding considerable uncertainty to the measurements. The present invention may be equivalently employed for any device for shortening animal nails, including but not limited to clippers, trimmers, scissors, cutters, shavers, grinders, filers, and so forth.

It may be desirable to miniaturize and integrate the optical source, optical sensor, power source, processor components, and indicator so that they may be integrated with the nail clipper (embedded within a handle, for example). The present invention may be implemented as an already-integrated product, or as add-on component(s) for an existing nail clipper. The present invention may also be implemented with one or more of the optical source(s), optical sensor(s), power source, processor, and indicator provided as separate components connected to the nail clipper by optic and/or electronic links.

Apparatus and methods according to the present invention may be employed for locating living tissue within the nail and/or the end of the animal's digit within the nail for reasons other than trimming the nail. It may be desirable or necessary to reliably locate living tissue within the nail and/or to accurately locate the end of the animal's digit within the nail for a variety of diagnostic and/or therapeutic veterinary procedures, for example. Any methods and apparatus according to the present invention may be employed for such purposes, and such use shall fall within the scope of inventive concepts disclosed and/or claimed herein.

The present invention has been set forth in the forms of its preferred and alternative embodiments. It is nevertheless intended that modifications to the disclosed optical source and sensor for animal nail clippers may be made without departing from inventive concepts disclosed and/or claimed herein.

What is claimed is:

1. A method, comprising:
   a) selectively illuminating a portion of an animal nail with an optical source;
   b) collecting light from the selectively-illuminated portion of the animal nail and transmitting at least a portion of the collected light to an optical sensor, thereby generating an optical signal level;
   c) comparing the generated optical signal level to a quick-signal-level range and to a nail-signal-level range, a generated optical signal level in the quick-signal-level range arising from a selectively-illuminated living-tissue-containing portion of the animal nail, a generated optical signal level in the nail-signal-level range arising from a selectively-illuminated portion of the nail substantially devoid of living tissue; and
   d) indicating to a user whether the generated optical signal level is within the quick-signal-level range or within the nail-signal-level range,
   wherein the optical source and the optical sensor are operatively coupled to an animal nail clipper and positioned so that when the generated optical signal level is within the nail-signal-level range and the clipper is actuated to cut the nail, cutting of the living-tissue-containing portion of the animal nail is substantially avoided.

2. The method of claim 1, further comprising actuating the nail clipper to cut the nail when the generated optical signal level is within the nail-signal-level range.

3. The method of claim 1, wherein the generated optical signal level arises from wavelength-selective illumination of the animal nail.

4. The method of claim 3, wherein the optical source comprises at least one light-emitting diode.

5. The method of claim 3, wherein the optical source comprises at least one laser source.

6. The method of claim 3, wherein the optical source comprises a broadband optical source and at least one wavelength-selective optical component.

7. The method of claim 1, wherein the optical sensor includes at least one wavelength-selective optical component.

8. The method of claim 1, wherein the generated signal level arises from multiple-wavelength illumination of the animal nail.

9. The method of claim 8, wherein:
   the optical source comprises at least one broadband optical source; and
   the optical sensor comprises multiple optical sensors and at least one wavelength-selective optical component.

10. The method of claim 8, wherein:
    the optical source comprises multiple narrowband optical sources; and
    the optical sensor comprises multiple optical sensors.

11. The method of claim 10, wherein the multiple optical sensors include at least one wavelength-selective optical component.

12. The method of claim 8, wherein:
    the optical source comprises multiple narrowband optical sources; and
    the optical sensor receives collected light at multiple wavelengths from the illuminated portion of the animal nail.

13. The method of claim 1, wherein the optical source and the optical sensor are positioned and aligned relative to the nail clipper so that when the generated signal level is within the nail-signal-level range and the clipper is actuated to cut the nail, cutting of the living-tissue-containing portion of the animal nail is substantially avoided.

14. The method of claim 1, wherein:
    the optical source includes a corresponding source optical fiber segment having a proximal end for receiving light from the optical source and a distal end for emitting light from the optical source and selectively illuminating a portion of the animal nail;
    the optical sensor includes a corresponding sensor optical fiber segment having a distal end for collecting light from the selectively illuminated portion of the animal nail and a proximal end for transmitting at least a portion of the collected light to the optical sensor; and
    the corresponding distal ends of the source optical fiber segment and the sensor optical fiber segment are positioned and aligned relative to the to the nail clipper so that when the generated optical signal level is within the nail-signal-level range and the nail clipper is actuated to cut the nail, cutting of the living-tissue-containing portion of the animal nail is substantially avoided.

15. The method of claim 1, wherein:
    the optical source includes at least one corresponding source optical component for directing light from the optical source for selectively illuminating the portion of the animal nail;
    the optical sensor includes at least one corresponding sensor optical component for collecting light from the selectively illuminated portion of the animal nail and transmitting the collected light to the optical sensor; and
    the source optical component and the sensor optical component are positioned and aligned relative to the to the nail clipper so that when the generated signal level is within the nail-signal-level range and the clipper is actuated to cut the nail, cutting of the living-tissue-containing portion of the animal nail is substantially avoided.

16. The method of claim 1, wherein:
    the optical source is a pulsed optical source; and
    the generated optical signal is processed by gated detection, the gated detection and the pulsed optical source being commonly triggered.

17. The method of claim 1, wherein:
    the optical source is a modulated optical source,
    generated optical signal is processed by phase-sensitive detection, the modulated optical source and the phase sensitive detection being commonly synchronized.

18. The method of claim 1, wherein a generated optical signal level in the nail-signal-level range is indicated by a first indication of a binary indicator, and a generated optical signal level in the quick-signal-level range is indicated by a second indication of the binary indicator.

19. The method of claim 1, wherein a level indicator indicates which of multiple indicator signal levels most closely approximates the generated optical signal level, the multiple indicator signal levels spanning a signal level range including at least a portion of the quick-signal-level range and at least a portion of the nail-signal-level range.

20. The method of claim 1, further comprising: repeating steps a) through d) at multiple locations along the nail, thereby substantially determining the location of a distal end of the living tissue within the animal nail.

* * * * *